(12) United States Patent
Kalkhoran et al.

(10) Patent No.: US 8,003,551 B2
(45) Date of Patent: *Aug. 23, 2011

(54) SURFACE-ACTIVATION OF SEMICONDUCTOR NANOSTRUCTURES FOR BIOLOGICAL APPLICATIONS

(75) Inventors: Nader Montazernezam Kalkhoran, Tewksbury, MA (US); James G. Moe, Sudbury, MA (US); Kurt J. Linden, Wayland, MA (US); Marisa Sambito, Bedford, MA (US)

(73) Assignee: Spire Corporation, Bedford, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/430,464

(22) Filed: Apr. 27, 2009

(65) Prior Publication Data

US 2009/0224216 A1     Sep. 10, 2009

Related U.S. Application Data

(63) Continuation of application No. 11/002,851, filed on Nov. 30, 2004, now Pat. No. 7,524,776.

(51) Int. Cl.
*H01L 21/3065* (2006.01)
(52) U.S. Cl. ......... 438/798; 257/E21.218; 257/E21.311; 257/E21.334; 438/712; 438/788; 438/960; 977/774; 977/786; 977/888
(58) Field of Classification Search ........... 257/E21.218, 257/E21.311, E21.334; 438/409, 712, 960, 438/788, 792, 798; 977/773, 774, 786, 814, 977/888, 899
See application file for complete search history.

(56) References Cited

U.S. PATENT DOCUMENTS

| | | | |
|---|---|---|---|
| 5,427,648 A | 6/1995 | Pamulapati et al. |
| 6,235,618 B1 | 5/2001 | Jeong-Sook et al. |
| 6,444,143 B2 | 9/2002 | Bawendi et al. |
| 6,514,772 B2 | 2/2003 | Siiman et al. |
| 6,548,264 B1 | 4/2003 | Tan et al. |
| 6,585,947 B1 | 7/2003 | Nayfeh et al. |

(Continued)

FOREIGN PATENT DOCUMENTS

WO    WO-03/087291 A2    10/2003

OTHER PUBLICATIONS

Bley et al, Characterization of Silicon Nanoparticles Prepared from Porous Silicon, Chem. Mater. 1996, 8, 1881-1888.*

(Continued)

*Primary Examiner* — Anh Phung
*Assistant Examiner* — Michael Lulis
(74) *Attorney, Agent, or Firm* — Thomas J. Engellenner; Reza Mollaaghababa; Nutter McClennen & Fish LLP

(57) ABSTRACT

The present invention provides means and methods for producing surface-activated semiconductor nanoparticles suitable for in vitro and in vivo applications that can fluoresce in response to light excitation. Semiconductor nanostructures can be produced by generating a porous layer in semiconductor substrate comprising a network of nanostructures. Prior or subsequent to cleavage from the substrate, the nanostructures can be activated by an activation means such as exposing their surfaces to a plasma, oxidation or ion implantation. In some embodiments, the surface activation renders the nanostructures more hydrophilic, thereby facilitating functionalization of the nanoparticles for either in vitro or in vivo use.

19 Claims, 2 Drawing Sheets

U.S. PATENT DOCUMENTS

| | | |
|---|---|---|
| 6,623,559 B2 | 9/2003 | Huang |
| 6,632,694 B2 | 10/2003 | Torvik |
| 6,649,138 B2 | 11/2003 | Adams et al. |
| 7,306,963 B2 | 12/2007 | Linden |
| 7,524,776 B2 * | 4/2009 | Kalkhoran et al. ........... 438/798 |
| 2002/0132101 A1 | 9/2002 | Fonash et al. |
| 2004/0229447 A1* | 11/2004 | Swihart et al. ................ 438/507 |
| 2005/0233487 A1 | 10/2005 | Liu et al. |

OTHER PUBLICATIONS

Zhang et al., Luminescent Si Nanoparticles in Sol-Gel Matrices Stabilized by Amino Acids, Chem. Mater. 1997, 9, 2249-2251.*

U.S. Appl. No. 10/120,974, Roger G. Little.

Heinrich et al., Luminescent Colloidal Silicon Suspensions from Porous Silicon, Science, vol. 255, pp. 66-68.

* cited by examiner

US 8,003,551 B2

SURFACE-ACTIVATION OF SEMICONDUCTOR NANOSTRUCTURES FOR BIOLOGICAL APPLICATIONS

CROSS-REFERENCE TO RELATED APPLICATIONS

This application is a continuation of U.S. patent application Ser. No. 11/002,851, filed Nov. 30, 2004, now U.S. Pat. No. 7,524,776, and entitled "SURFACE-ACTIVATION OF SEMICONDUCTOR NANOSTRUCTURES FOR BIOLOGICAL APPLICATIONS," the teachings of which are hereby incorporated by reference.

FIELD OF THE INVENTION

This application relates to the production of semiconductor nanoparticles, and in particular to the production of surface-activated biocompatible semiconductor nanoparticles.

BACKGROUND OF THE INVENTION

Semiconductor nanoparticles, or quantum dots, are nanometer or micrometer-sized semiconductor structures in which one to a few thousand charge carriers, e.g., electrons, are confined, giving them a unique ability to emit visible or near infrared (IR) photons within a very narrow spectrum and with high efficiency. Because of this, semiconductor nanoparticles can be useful in numerous biological, genomic and proteomic applications, for example, as markers, as components of microchip arrays (biochips), and as conjugates for fluoroimmunoassays for in vitro and in vivo molecular imaging studies.

At present, fluorophores synthesized from organic molecules typically are used in such applications. While organic fluorophores have had some success, they tend to be unstable and gradually degrade when exposed to blue or UV excitation light, in a phenomenon known as photobleaching, or simply degrade with time. Further, such molecules typically emit light in the normal visible region, similar to that of other materials used in biological applications, resulting in a poor signal to noise ratio. Organic fluorophores that emit light in the near-infrared region are not generally commercially available and, hence, difficult to obtain.

Inorganic semiconductor nanoparticle materials synthesized from CdSe and ZnS-based materials are also used in biological, genomic and proteomic applications. Because such inorganic materials can be toxic when used in vivo, a coating of a protective material usually is necessary to render them useful in biological applications. However, as a result of the coating, which absorbs and/or reflects light, the fluorescent properties of the material are diminished.

Moreover, many inorganic nanostructures are hydrophobic by nature and consequently are not easily dissolved or suspended in aqueous solutions, rendering their use difficult in various applications, both in vitro and in vivo. Accordingly, there remains a need for better semiconductor nanoparticles, especially for use in fluorescence-based biological applications.

SUMMARY OF THE INVENTION

The present invention generally provides methods for producing surface-activated semiconductor nanoparticles that exhibit colloidal stability and can be adapted for use in vitro and/or in vivo. Various methods are disclosed for activation of the surface of quantum dot structures to render them more hydrophilic or to otherwise make them more suitable for use with aqueous carriers and/or more easily functionalized or conjugated with biological materials or reagents. Surface activation can be conducted via ion treatment, plasma treatment or oxidation as an intermediate step in the production of the quantum dots or subsequent to initial harvesting of the semiconductor particles.

In one aspect, the present invention provides a method of producing semiconductor nanostructures by generating a plurality of nanostructures and activating their surfaces to render them more hydrophilic. The activation of the surfaces can be achieved, for example, by exposure of the nanostructures to ECR plasma, oxidation or ion implantation.

In another aspect, semiconductor nanoparticles can be formed by (1) generating a porous semiconductor layer on a substrate, said porous layer including a plurality of porous nanostructures; (2) cleaving the nanostructures to generate a plurality of semiconductor nanoparticles; and (3) activating at least a portion of a surface of the nanoparticles to enhance hydrophilicity thereof. The semiconductor can be an element, such as silicon, or a compound, such as GaAs. Porosity can be achieved by chemical or electrochemical etching. Cleavage can be induced, for example, by sonication and, again, surface activation can occur before or after cleavage. Alternatively, the activation step can be performed before cleaving the nanostructures from the substrate.

In another aspect, semiconductor nanoparticles can be produced by (1) depositing a release layer on a semiconductor substrate; (2) forming a heterostructure over the release layer; (3) applying a plurality of masking nanoparticles to portions of the surface of the heterostructure such that part of the surface of the heterostructure can be selectively etched; (4) removing the exposed portion of the heterostructures wherein a plurality of nanostructures are formed attached to the release layer; (5) activating at least a portion of a surface of the nanostructures to enhance their hydrophilicity; and (6) dissolving the release layer whereby semiconductor nanoparticles are formed. The nanostructures can be activated by exposure to an ECR plasma, oxidation or ion implantation, and the activation step can also occur after the release layer is dissolved and the semiconductor nanoparticles are formed.

The activated semiconductor nanoparticles are formed, they can be functionalized with a biomaterial. For example, the biomaterial can be a biocompatible coating, a binding agent or a ligand. The functionalized particles can then be used for diagnostic, imaging and/or therapeutic purposes. Alternatively, the activated nanoparticles can be disposed in an aqueous medium so as to generate a colloidal suspension.

DETAILED DESCRIPTION OF THE INVENTION

In one aspect, the present invention provides methods for producing surface-activated semiconductor nanoparticles suitable for in vitro and in vivo applications which can fluoresce in response to light excitation. The terms "quantum dots," "nanostructures" and "nanoparticles" are used interchangeably herein to describe compositions on the order of less than a nanometer to a few micrometers in size, and more preferably from about 1 to about 100 nanometers of active device structure, that possess optical properties derived from excitation of a confined population of charge carriers.

The semiconductor nanostructures of the present invention can be activated in various ways, such as by exposing their surfaces to a plasma, oxidation or ion bombardment. Once the surface is activated, functionalization of the nanoparticle for either in vitro or in vivo use can occur.

So that the invention is more clearly defined, "activated" semiconductor nanostructures or "activated" semiconductor nanoparticles are compositions that have modified surface characteristics, e.g., more hydrophilic or hydrophobic, which facilitates functionalization or enhances colloidal stability.

In one embodiment, semiconductor nanostructures having activated surfaces can be generated by etching a surface of a semiconductor wafer, e.g., via an anodic etching process such as that described in more detail below, to generate a surface layer comprising a nanostructured porous network. The porous network can be subjected to an activation step, e.g., via exposure to an ECR plasma or ion implantation, to activate surfaces of the nanostructures forming the porous network. These activated nanostructures can be released as nanoparticles having activated surfaces by employing a variety of techniques, e.g., sonication of the porous layer. Alternatively, prior to forming the porous layer, the semiconductor surface can be activated, e.g., via ion implantation, followed by generating the porous layer and releasing the nanostructures.

Figure 1:
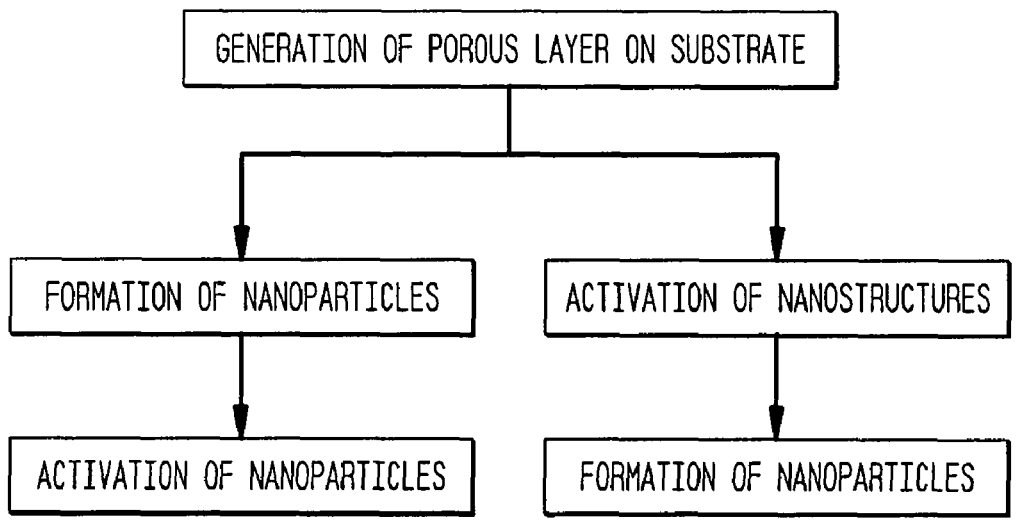
FIG. 1 is a schematic flow diagram illustrating the various steps performed by one embodiment of a method according to the teachings of the present invention for creating surface-activated biocompatible fluorescent semiconductor nanoparticles by formation on a porous substrate.

By way of example, and as shown in a schematic flow diagram of FIG. 1, semiconductor nanoparticles can be formed by generating a porous silicon layer over a semiconductor substrate. The substrate can be any suitable semiconductor material known in the art, such as silicon, germanium, various compounds of Group III-V elements, or combinations thereof. In a preferred embodiment, the semiconductor material is preferably an n-type (phosphorus doped) or p-type (boron doped) single-crystal silicon wafer. Further, the single crystal silicon can have any suitable crystallinity, but is preferably has a (001) lattice orientation.

Figure 2:
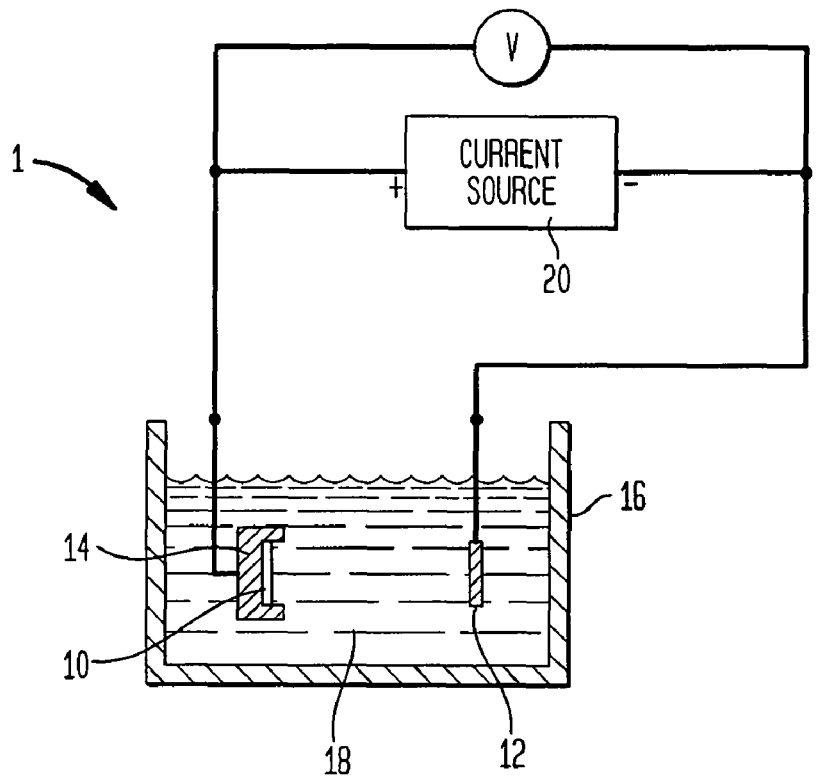
FIG. 2 is a schematic illustration of an etching system for generating porous silicon substrates suitable for use with the present invention.

For example, in an initial step, a bulk substrate can be etched so as to generate a nanostructured porous surface layer. FIG. 2 shows an exemplary etching system 1 for generating porous silicon substrates 10 suitable for use with the present invention that includes a cathode 12, and an anode 14 disposed in a vessel 16, e.g., a Teflon vessel. The vessel can contain a suitable electrolyte 18, for example, a mixture of HF and ethanol, for anodically etching a surface of the silicon substrate, which is positioned in the holder such that one surface thereof is exposed to the electrolyte solution while the other surface is isolated therefrom. A current source 20 generates a current flowing through the electrolyte solution to cause etching of the substrate's exposed surface. The etching process can sometimes be enhanced if the exposed surface of the silicon substrate is first doped, e.g., doped with boron to render it a p-type semiconductor. The porous layer can include a network of nanostructures that can be activated and released as discussed in more detail below.

A person skilled in the art will appreciate that adjustments to the anodization conditions, such as the HF concentration, the pH of the solution and its chemical composition, current density, temperature, etching time, stirring conditions and illumination during the etching process, can result in the porous silicon layer exhibiting various properties. For example, the use of an alcohol solution (e.g., a 1:1 ethanol HF solution) may be preferable because it can reduce the formation of hydrogen bubbles at the substrate surface, thereby facilitating production of a more uniform porous silicon layer.

Following formation, the semiconductor nanostructures can be cleaved from the substrate using any method known in the art to yield fluorescent semiconductor nanoparticles. For example, in a preferred embodiment, the semiconductor nanostructures can be cleaved by sonication as taught in U.S. Pat. No. 6,585,947, herein incorporated by reference. Alternatively, the semiconductor nanostructures can be cleaved to form semiconductor nanoparticles by shaking, scraping, pounding or any other technique whereby the semiconductor nanostructures can be separated from the substrate. In some embodiment, following cleavage, the semiconductor nanoparticles can be filtered using a commercial filter so as to remove any residual clusters and obtain nanoparticles having substantially uniform sizes in at a desired value or in a desired range.

Referring again to the flow chart of FIG. 1, the surfaces of the cleaved nanostructures can be activated to modulate their surface properties, for example, to render them more hydrophilic. Although in this exemplary embodiment, activation of the surfaces is performed following cleavage of the nanostructures from the porous layer, in other embodiments, the nanostructured can be activated while connected in the porous network, and then cleaved.

Such activation can result in semiconductor nanostructures that exhibit colloidal stability and have increased hydrophobic or hydrophilic affinities. Generally speaking, a "hydrophobic" compound is one that lacks an affinity for polarized solutions, such as those containing water; a "hydrophilic" compound is one that has an affinity for polarized solutions, such as those containing water.

In one embodiment of the present invention, a plasma treatment technique is used to activate the surface of the semiconductor nanostructures. By way of a non-limiting example, one type of plasma treatment technique that can be employed in the practice of the present invention is electron cyclotron resonance (ECR), which allows a surface to be modified via exposure to a spatially localized gaseous plasma.

In general, an ECR plasma can be generated by providing a static magnetic field having a selected strength, i.e., amplitude, within a region of space in which a quantity of gas is contained, or through which the gas is flowing. The gas is then irradiated with electromagnetic radiation having a frequency which is substantially equal to ECR frequency at the applied magnetic field strength, and causes the gas to ionize, thus producing a plasma. A surface to be treated is exposed to an ECR-generated plasma for a time period ranging from about one second to about one minute. While different exposure times can be selected for different modifications of the surface, for example, shorter exposure times, such as one second, can be sufficient to activate the surface of the nanostructures.

Any combination of the radiation frequency and magnetic field amplitude that substantially satisfy the following equation (Equation 1) can be used to obtain an ECR-generated plasma in accord with the teaching of the invention:

$$F_c = 1/2\pi * (eB/m)$$ Equation (1)

where $f_c$ denotes the ECR frequency, B denotes the amplitude of the magnetic field, and e and m denote the charge and the mass of an electron, respectively. However, while various radiation frequencies and magnetic field strengths can be utilized to create and ECR-generated plasma, in a preferred embodiment, the radiation frequency can be selected to be in a range of about 1 GHz to about 15 GHz, and the applied static magnetic field can be selected to have an amplitude in a range of approximately 300 Gauss to approximately 5500 Gauss. By way of a non-limiting example, in one embodiment of the invention, the frequency of the electromagnetic radiation can be about 2.45 GHz and the amplitude of the applied magnetic field can be approximately 875 Gauss. Alternatively, the frequency of the electromagnetic radiation can be about 10 GHz when the amplitude of the applied magnetic field is approximately 3571 Gauss.

Additionally, a variety of gasses and gas pressures can be used in conjunction with the magnetic field when forming an ECR plasma. These gases include, but are not limited to, noble gases, such as argon, diatomic gases, such as oxygen and nitrogen, hydrocarbons, such as methane and butane, and fluorinated hydrocarbons, such as tetrafluoromethane. Moreover, various mixtures of different gases can be utilized to create an ECR plasma in accordance with the teachings of the invention. For example, a mixture of argon and oxygen (e.g., a mixture having 50% molar concentration of argon and 50% molar concentration of oxygen) or a mixture of argon and ammonia can be used. Additionally, the gas pressure can be in a range of about 0.1 Pa to about 1000 Pa, preferably in the range of about 1 Pa to about 10 Pa, and most preferably about 2 Pa to about 8 Pa.

In one embodiment of the present invention, ion treatment can be used to activate the surface of the semiconductor nanostructures. The term "ion treatment" and similar wording as used herein is intended to encompass ion implantations, ion depositions, ion-beam-assisted deposition and ion-enhanced sputtering. As used in the present invention, ion treatment refers to any treatment of a surface location (called a "localized area") by utilizing energized ions. For example, an ion-beam-assisted deposition (IBAD) process can be employed in which an ion source can accelerate ions into selected portions of a substrate for implantation therein. U.S. Pat. No. 5,520,664, herein incorporated by reference, provides further details regarding IBAD process and apparatus thereof.

The implanted ions can modify one or more surface properties of the nanostructures to modulate, e.g., enhance, their affinity for functionalization relative to an nanostructure surface not treated with ions. Alternatively, activation of the semiconductor nanostructures can occur by an ion implantation technique in which a selected number of localized areas are formed on a substrate surface by implanting one ion type in certain discrete regions of the substrate while other localized areas are formed on the substrate surface by implanting another ion type in other discrete regions. This results in a substrate having two types of localized areas, such that various localized areas have different surface properties relative to one another and/or relative to the remainder of the substrate surface.

In general, surface activation results in a desired modification of the nanoparticles' surface properties. One such modification can be a change in hydrophilicity or hydrophobicity. The term "hydrophilic" and its derivatives are used herein to describe materials that have an affinity for water and/or are capable of being dispersed in water. One measure of a hydrophilic material is its ability to transfer from a non-aqueous to an aqueous phase in a dual phase system. For example, a "hydrophilic" compound typically will transfer from an organic phase to an aqueous phase, specifically from an organic, water-immiscible nonpolar solvent (e.g., with a dielectric constant less than 5) to water, with a partition coefficient or greater than about 50%. The term "water-dispersible" particles as used herein refers to an essentially unaggregated dispersion of particles, such that discrete particles of approximately 1 nm to 500 nm can be sustained indefinitely at high concentrations (10-20 microMolar).

Any ion that is amenable to implantation in a given surface and that leads to a desired surface modification can be utilized for surface activation including, by way of a non-limiting example, nitrogen, oxygen, argon, carbon, fluorine, chlorine, hydrogen and helium. Further, the dose of the implanted ions at each localized area should be sufficient to activate the area, and can be in a range of about $10^{12}$ to about $10^{17}$ ions/cm$^2$. More preferably, the dose can be in a range of about $10^{14}$ to about $10^{16}$ ions/cm$^2$. For example, a dose of nitrogen ions in a range of about $10^{15}$ to about $10^{16}$ ions/cm$^2$ can be implanted at selected surface positions to provide a plurality of localized areas which are more hydrophilic than the remainder of the substrate surface. Alternatively, a dose of fluorine ions in a range of about $10^{12}$ ions/cm$^2$ to about $5 \times 10^{17}$ ions/cm$^2$ can be utilized to create localized areas that are more hydrophobic than the remainder of the surface.

Alternatively, ion bombardment of selected positions on a substrate to implant a selected ion at a specific position can be used to activate the surface of the nanostructures. More particularly, in one such method, initially, a mask is disposed over the substrate. The mask permits selective treatment of the substrate surface, for example by an ion beam. A variety of masks can be utilized to selectively expose different portions of a substrate surface to the ion beam. For example, the mask can be formed of silicon dioxide ($SiO_2$). The mask can be deposited on a silicon substrate, for example, by utilizing chemical vapor deposition (CVD) to deposit a masking layer that can be patterned by employing a number of known methods, such as photolithography. The patterned mask can provide a plurality of exposed and unexposed portion. The substrate can then be exposed to a beam of ions, such as nitrogen ions, having a selected energy based on a particular application (e.g., an ion energy in a range of about 0.1 keV to about 1000 keV) so as to implant a selected dose of ions in the exposed portions. A person skilled in the art will appreciate the variety of ion implantation systems that can be employed for activating the surface of the semiconductor nanostructures. The portion of the substrate implanted with ions can be rendered porous, e.g., by employing an etching technique such as that described above, to form a network of nanostructures that can be released, e.g., via sonication, to generate a plurality of nanoparticles having activated surfaces due to the presence of the implanted ions.

In another embodiment of the present invention, the surface of the semiconductor nanostructures can be activated by oxidation. While a variety of oxidation techniques can be used, the oxidation technique should preferably activate the surface of the semiconductor nanostructures, while being controlled to such an extent that the oxidized semiconductor nanostructures would retain their fluorescent properties. By way of a non-limiting example, the oxidation technique can include exposing the semiconductor nanostructures to an oxidizing atmosphere at an elevated temperature. While the oxidizing atmosphere can have a variety of compositions, in a preferred embodiment, it contains at least about 1% $O_2$. Alternatively, the oxidizing technique can include immersing the semiconductor nanostructures in an oxidizing solution for a length of time such that oxidation occurs. While the oxidizing solution can have a variety of compositions, a preferred oxidizing solution contains at least a percentage of sodium peroxide, nitric acid or sulfurous acid. Additionally, the length of the immersion time can vary in accordance with the properties of the oxidizing solution, for example and as shown by U.S. Pat. No. 6,649,138, herein incorporated by reference, approximately 45 minutes to 1 hour is a suitable time frame for immersion in an $H_2O_2$ oxidizing solution so that the surface is oxidized at one monolayer thick.

While the semiconductor nanostructures formed by the above methodologies can be cleaved to form semiconductor nanoparticles that have a variety of average sizes, in a preferred embodiment, the average maximum dimension of the semiconductor nanoparticles is preferably between about 0.5 nm to about 25 nm, and more preferably between about 2 nm to about 10 nm. Further, while the absorption and emission maximum of the semiconductor nanoparticles can vary, in one preferred embodiment the absorption and emission maxima are between about 400 nm and about 1200 nm, more preferably between about 500 nm and about 900 nm and, by way of example, between about 500 nm to 600 nm, about 600 nm to 700 nm, about 700 nm to 800 nm or about 800 nm to 900 nm. In an exemplary embodiment, the semiconductor nanoparticles have a narrow emission spectrum (less than 75 nm, more preferably less than 50 nm) and a spectral separation between the absorption and emission spectra of more than about 20 nm, but preferably no more than about 50 nm.

One skilled in the art will appreciate that a variety of techniques can be employed to form semiconductor nanostructures for use in accordance with the present invention. For example, further techniques for forming semiconductor heterostructures and then producing quantum dot nanostructures by etching and then releasing individual nanoparticles are taught in co-pending commonly owned U.S. patent application entitled "Precision Synthesis of Quantum Dot Nanostructures for Fluorescent and Optoelectronic Device," filed on even date herewith and incorporated by reference.

Figure 3:
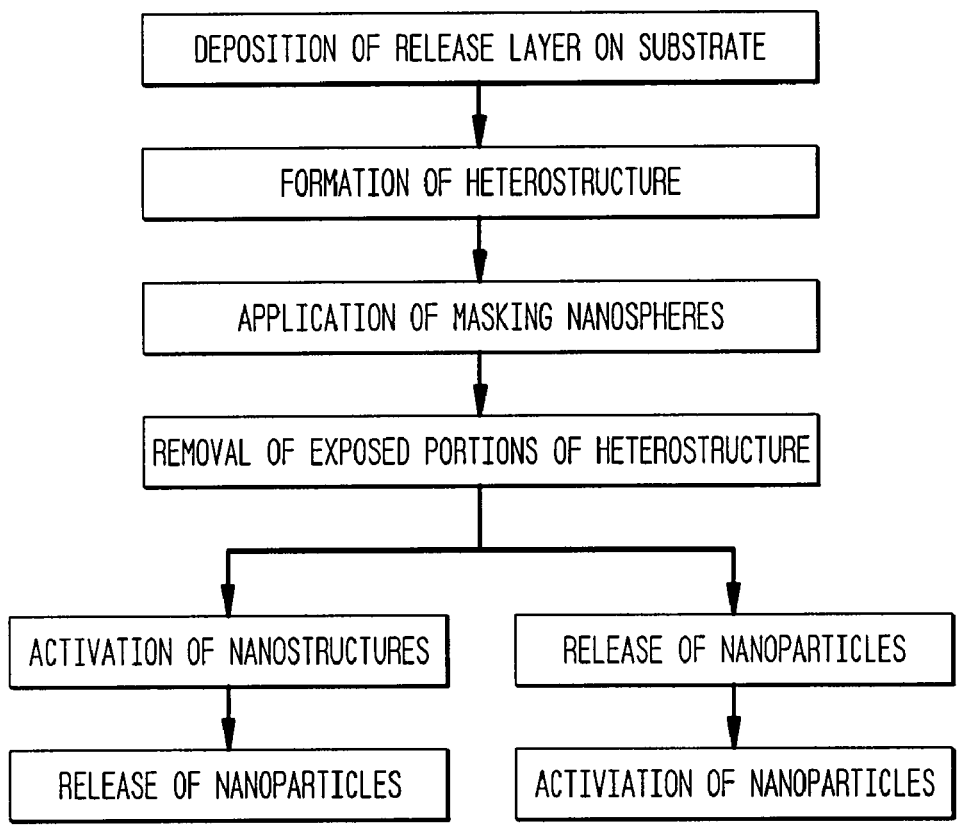
FIG. 3 is a schematic flow diagram illustrating the various steps performed by another embodiment of a method according to the teachings of the present invention for creating surface-activated biocompatible fluorescent semiconductor nanoparticles via epitaxial deposition techniques.

By way of example, FIG. 3 presents a schematic flow diagram depicting a process in accordance with another embodiment the present invention in which semiconductor epitaxial deposition techniques, together with the teachings of the invention, can be used to generated activated semiconductor nanoparticles. More specifically, semiconductor nanoparticles are formed by depositing a release layer on a semiconductor wafer followed by deposition of additional layers that form a heterostructure. A plurality of ion-blocking nanospheres are then disposed on the surface of the heterostructure and the surface of the heterostructure is etched to remove the exposed portions, resulting in the formation of semiconductor nanoparticles.

Figure 4:
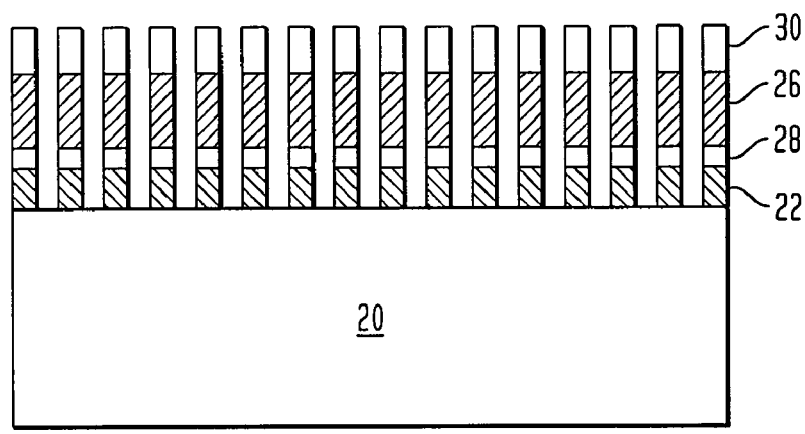
FIG. 4 illustrates a heterostructure formed on a wafer in accordance with one embodiment of the present invention.

As shown in FIG. 4, a release layer 22 is deposited upon the semiconductor wafer, which can be any suitable semiconductor so long as it is able to generate nanoparticles suitable for optical or optoelectric applications. The semiconductor wafer preferably incorporates Group III-V elements, such as GaAs, InGaAs or AlGaAs. Alternatively, the semiconductor wafer can be made of silicon or germanium. Additionally, while the release layer may be made of a variety of materials, it should be of such material that can be evenly deposited and easily dissolved, such as, other Group III-V elements, or dielectric materials deposited upon the substrate as pseudomorphic layers. For example, in one embodiment, the release layer is formed of AlAs. Those skilled in the art will appreciate that rather than utilizing InGaAs and GaAs for forming the heterostructure layer, other semiconductor materials, particularly other Group III-V elements, can be used. More generally, semiconductors useful in producing the quantum dots of the present invention can include II-VI, III-V and group IV semiconductors. (Alternatively, using the new IUPAC system for numbering element groups, suitable semiconductor materials include, but not limited to, the following: materials comprised of a first element selected from Group 2 or 12 of the Periodic Table of the Elements and a second element selected from Group 16 (e.g., ZnS, ZnSe, ZnTe, CdS, CdSe, CdTe, HgS, HgSe, HgTe, MgS, MgSe, MgTe, CaS, CaSe, CaTe, SrS, SrSe, SrTe, BaS, BaSe, BaTe, and the like); materials comprised of a first element selected from Group 13 of the Periodic Table of the Elements and a second element selected from Group 15 (GaN, GaP, GaAs, GaSb, InN, InP, InAs, InSb, AlS, AlP, AlAs, AlSb, and the like); materials comprised of a Group 14 element (Ge, Si, and the like); materials such as PbS, PbSe and the like; and alloys and mixtures (including ternary and quaternary mixtures) thereof.

The release layer can deposited upon the substrate by employing any deposition technique known in the art, e.g., chemical vapor deposition or molecular beam epitaxy. Following application of the release layer to the wafer, a heterostructure can be deposited on the release layer to provide at least one one-dimensional confinement of electrons or other charge carriers therein. As shown in FIG. 4, above the release layer 22, the heterostructure 24 includes a one-dimensional quantum well layer 26 sandwiched between the two confinement layers 28, 30 that provide confinement of selected charged carriers, such as electrons, within the quantum well layer 26. While the term "quantum well" is known in the art, to the extent that a definition may be needed, a "quantum well," as used herein, refers to a generally planar semiconductor region, having a selected composition, that is sandwiched between semiconductor regions having a different composition (typically referred to as barrier or confinement layers), selected to exhibit a larger bandgap energy than that of the composition of the quantum well layer 26. The spacing between the confinement layers 28, 30, and consequently the thickness of the quantum well layer 26, is selected such that charge carriers (e.g., electrons) residing in the quantum well layer 26 exhibit quantum effects in a direction perpendicular to the layer (e.g, they can be characterized by discrete quantized energy levels).

Such heterostructures can have varied dimensions that can be selected based on desired properties of semiconductor nanostructures, such as, a desired emission spectrum. The thickness of various layers forming the heterostructure should be selected to allow an ion beam, utilized in subsequent etching steps, to sufficiently penetrate and etch away selected portions of the heterostructure. Additionally, while the heterostructure can have a variety of heights, in an exemplary embodiment, the heterostructure has a height ranging from about 1 nm to about 10 nm, and preferably, a height of about 5 nm.

Referring back to FIG. 4, the quantum well layer 26 and the confinement layers 28, can be deposited on the wafer 20 by employing a variety of techniques, such as organic chemical vapor deposition (MOCVD), and/or plasma assisted molecular beam epitaxial growth. It will be appreciated that MOCVD is particularly suitable for depositing Group III-V semiconductor materials on the wafer. By way of example, commonly-owned U.S. Pat. No. 6,066,204, incorporated herein by reference, discloses methods and apparatus for epitaxial deposition techniques that can be utilized for generating the heterostructure layer 24.

In an exemplary embodiment, the one-dimensional quantum well layer 26 is formed of InGaAs while the confinement layers 28, 30 are formed of GaAs. The quantum well layer 26 can have a thickness in a range of about 1 nanometer to about a few hundred nanometers, and more preferably, in a range of about 2 nm to about 20 nm while each of the confinement layers 28, 30 can have a thickness in a range of about hundreds of nanometers.

Following formation of the heterostructure, and referring back to the schematic flow diagram of FIG. 3, a mask can be applied to a top surface of the heterostructure. For example, a plurality masking nanoparticles can be applied to an upper surface of the heterostructure to form a mask, e.g., a pattern of exposed and unexposed areas. In one embodiment, the mask protects part of the heterostructure from a subsequent etching step to which the wafer will be subjected, as described below.

While such mask can be formed by employing a variety of different techniques, in an exemplary embodiment the mask can be formed as a collection of gold or other metallic spheres having nanometer-sized radii that can be deposited on the top surface of the heterostructure so as to protect selected portions of the heterostructure from subsequent ion beam bombardment, described below, while leaving the other portions exposed. Additionally, the nanometer-sized mask particles can be formed from a variety of materials, however, such materials should inhibit occurrence of adverse affects during etching, such as oxidation and possible contamination of the wafer. Suitable mask materials for use with the present invention include gold in a colloidal solution that can be spread over a top surface of the heterostructure. Precision nanosized gold spheres suitable for use in practicing the methods of the invention can be obtained, for example, from Accurate Chemical Scientific Corporation of Westbury, N.Y. in 1, 5, 10, 15 and 20 nm sizes.

Following application of the ion-blocking nanospheres to the heterostructure, the surface of the heterostructure is etched so that a plurality of nanostructure elements are formed, each including a portion of the quantum well heterostructure disposed on a portion of the release layer. While the nanostructures can be formed by any technique known in the art, in a preferred embodiment, the nanostructures are formed by utilizing reactive ion etching or reactive ion beam etching.

Following irradiation, the release layer can be dissolved, if desired, to release the individual nanostructures forming semiconductor nanoparticles. (If the mask particles have not been eroded away during ion etching, the mask remnants can be removed at this time also.) While the release layer and the mask materials can be removed by a variety of techniques, by way of a non-limiting example, the release layer and/or the mask can be removed by dissolution in a suitable solvent, e.g., HF.

The surfaces of the released nanostructured can be activated by employing the techniques described above, e.g., by immersion in an oxidizing solution. Alternatively, after deposition of the release layer and the heterostructure layer, the heterostructure layer can be bombarded with ions to implant a selected ion dose therein. Subsequent processing steps can be followed as described above to generate nanostructure with activated surfaces due to the presence of the implanted ions.

Following activation of the nanostructures and cleavage to form semiconductor nanoparticles or following activation of already-cleaved semiconductor nanoparticles, the surface of the semiconductor nanoparticles can then be functionalized with binding agent or ligand, e.g., a biomaterial that can form a biocompatible coating over the activated surface.

The ligands can be attached to the activated surfaces via chemical bonds, such as polar or non-polar covalent bonds, as well as non-covalent bonds, ion bonds, metallic bonds, van der Waals interactions, or by cross-linking and caging.

In one embodiment, the surface-activated semiconductor nanoparticles can be disposed in a medium, so as to form a long term suspension. The medium can be any substance that can serve as a carrier for the semiconductor nanoparticles and not affect their fluorescent properties. In one preferred embodiment, the medium is water based. Additionally, while the semiconductor nanoparticles can be dispersed throughout the suspension in a variety of densities, in a preferred embodiment, the density of the nanoparticles can be in a range of about 1 microgram to about 10 milligrams per milliliter.

One skilled in the art will appreciate further features and advantages of the invention based on the above-described embodiments. Accordingly, the invention is not limited by what has been particularly shown and described, except as indicated by the appended claims. All publications and references cited are expressly incorporated herein by reference in their entirety.

What is claimed is:

1. A method for generating a plurality of nanoparticles comprising:
   forming a porous semiconductor layer on a substrate, said porous layer including a plurality of semiconductor nanostructure elements;
   cleaving said nanostructure elements to generate a plurality of nanoparticles; and
   activating at least a portion of a surface of the nanoparticles;
   wherein the step of generating a porous semiconductor layer comprises subjecting a silicon susbtrate to reactive ion etching.

2. The method of claim 1, wherein the cleaving step comprises sonicating the porous nanostructure elements.

3. The method of claim 1, further comprising the step of coating the nanoparticles with a biocompatible coating.

4. The method of claim 3, wherein the coating is an organic coating.

5. The method of claim 1, wherein the nanoparticles have an average maximum dimension between about 5nm and about 100 nm.

6. The method of claim 1, further comprising attaching a ligand to the activated surface of the nanoparticle.

7. The method of claim 1, wherein the step of activating the surface portion further comprises increasing the surface hydrophilicity of the nanoparticles.

8. The method of claim 1 wherein the step of activating at least a portion of a surface of the nanoparticles further comprises exposing the nanoparticles to an oxidizing agent.

9. The method of claim 8 wherein the oxidizing agent is a solution comprising nitric acid.

10. The method of claim 1 comprising activating at least a portion of a surface of the nanoparticles to enhance the hydrophilicity thereof and disposing said nanoparticles in an aqueous solvent so as to generate a colloidal suspension of said particles.

11. The method of claim 10, wherein a density of said nanoparticles in the colloidal suspension is in a range of about 1 microgram to about 10 milligrams per milliliter.

12. The method of claim 1, wherein the step of activating at least a portion of a surface of the nanoparticles further comprises exposing the nanoparticles to a plasma.

13. The method of claim 12, wherein the plasma is formed from any of a noble gas, a diatomic gas, a hydrocarbon gas, and a fluorinated hydrocarbon gas.

14. A method for generating a plurality of nanoparticles comprising:
forming a porous semiconductor layer on a substrate, said porous layer including a plurality of semiconductor nanostructure elements;
cleaving said nanostructure elements to generate a plurality of nanoparticles; and
activating at least a portion of a surface of the nanoparticles;
wherein the step of activating at least a portion of a surface of the nanoparticles further comprises exposing the nanoparticles to an oxidizing agent;
wherein the oxidizing agent is an oxidizing atmosphere comprising at least 1 percent $O_2$.

15. A method for generating a plurality of nanoparticles comprising:
forming a porous semiconductor layer on a substrate, said porous layer including a plurality of semiconductor nanostructure elements;
cleaving said nanostructure elements to generate a plurality of nanoparticles, and
activating at least a portion of a surface of the nanoparticles;
wherein the step of activating at least a portion of a surface of the nanoparticles further comprises exposing the nanoparticles to an oxidizing agent;
wherein the oxidizing agent is a solution comprising sodium peroxide.

16. A method for generating a plurality of nanoparticles comprising:
forming a plurality of semiconductor nanostructure elements;
cleaving said nanostructure elements to generate a plurality of nanoparticles; and
activating at least a portion of a surface of the nanoparticles;
wherein the step of activating at least a portion of a surface of the nanoparticles further comprises exposing the nanoparticles to an oxidizing agent;
wherein the oxidizing agent is a solution comprising sulfurous acid.

17. A method for generating a plurality of nanoparticles comprising:
forming a porous semiconductor layer on a substrate, said porous layer including a plurality of semiconductor nanostructure elements;
cleaving said nanostructure elements to generate a plurality of nanoparticles; and
activating at least a portion of a surface of the nanoparticles to enhance the hydrophilicy thereof and disposing said nanoparticles in an aqueous solvent so as to generate a colloidal suspension of said particles;
wherein a density of said nanoparticles in the colloidal suspension is in a range of about 10 to 20 microMolar.

18. A method for generating a plurality of nanoparticles comprising:
forming a porous semiconductor layer on a substrate, said porous layer including a plurality of semiconductor nanostructure elements;
cleaving said nanostructure elements to generate a plurality of nanoparticles; and
activating at least a portion of a surface of the nanoparticles;
wherein the step of activating at least a portion of a surface of the nanoparticles further comprises exposing the nanoparticles to a plasma, and
wherein the plasma is formed from oxygen gas.

19. A method for generating a plurality of nanoparticles comprising:
forming a porous semiconductor layer on a substrate, said porous layer including a plurality of semiconductor nanostructure elements;
cleaving said nanostructure elements to generate a plurality of nanoparticles; and
activating at least a portion of a surface of the nanoparticles;
wherein the step of activating at least a portion of a surface of the nanoparticles further comprises exposing the nanoparticles to a plasma;
wherein the plasma is formed from any of a mixture of argon and oxygen and a mixture of argon and ammonia.

* * * * *